United States Patent [19]
Kehrbach et al.

[11] Patent Number: 5,843,948
[45] Date of Patent: Dec. 1, 1998

[54] PIPERAZINOPHENYL- AND PIPERAZINOPHENYLOXYCARBOXYLIC ACID DERIVATIVES, AND PROCESSES AND INTERMEDIATES FOR THEIR PREPARATION AND PHARMACEUTICAL COMPOSITIONS COMPRISING THEM

[75] Inventors: Wolfgang Kehrbach, Hanover; Uwe Schoen, Burgdorf, both of Germany; Jack A. J. den Hartog, Weesp, Netherlands; Jan H. van Maarseveen; Chris G. Kruse, both of Amersfoort, Netherlands; Jochen Antel, Bad Muender, Germany; Jan-Hendrik Reinders, Hilversum, Netherlands; Dieter Ziegler, Hemmingen; Gerhard-Wilhelm Bielenberg, Alfeld/Leine, both of Germany

[73] Assignee: Solvay Pharmaceuticals GmbH, Hanover, Germany

[21] Appl. No.: 994,754

[22] Filed: Dec. 19, 1997

[30] Foreign Application Priority Data

Dec. 19, 1996 [DE] Germany ............... 196 52 919.0

[51] Int. Cl.$^6$ ............... A61K 31/495; C07D 401/04; C07D 295/135
[52] U.S. Cl. ............... 514/252; 514/255; 544/360; 544/392
[58] Field of Search ............... 514/252, 255; 544/360, 392

[56] References Cited

U.S. PATENT DOCUMENTS 5,273,982 12/1993 Alig et al. ............... 514/315
5,442,064 8/1995 Pieper et al. ............... 544/360
5,563,268 10/1996 Linz et al. ............... 544/238

FOREIGN PATENT DOCUMENTS 0 542 363 A2 5/1993 European Pat. Off. .
93/14077 7/1993 WIPO .
96/24583 8/1996 WIPO .
97/02245 1/1997 WIPO .

OTHER PUBLICATIONS

Eldred et al., "Orally Active Non–Peptide Fibrinogen Receptor GpIIb/IIIa) Antagonists . . ." *J. Med. Chem.*, vol. 37:3882–85 1994).
Judkins et al., "A Versatile Synthesis of Amidines From Nitriles Via Amidoximes", *Synthetic Commun.*, vol. 26(23):4351–67 (1996).

*Primary Examiner*—Emily Bernhardt
*Attorney, Agent, or Firm*—Evenson, McKeown, Edwards & Lenahan, P.L.L.C.

[57] ABSTRACT

Compounds having fibrinogen receptor-antagonistic activity, of the general formula I

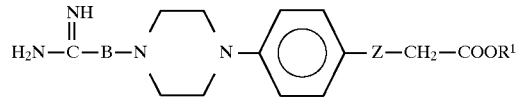

in which Z is oxygen or a methylene group, B is a phenyl or pyridyl radical, R$^1$ is hydrogen or a group forming a biolabile ester, and their physiologically acceptable acid addition salts and physiologically acceptable salts of acids of formula I.

12 Claims, No Drawings

PIPERAZINOPHENYL- AND PIPERAZINOPHENYLOXYCARBOXYLIC ACID DERIVATIVES, AND PROCESSES AND INTERMEDIATES FOR THEIR PREPARATION AND PHARMACEUTICAL COMPOSITIONS COMPRISING THEM

BACKGROUND OF THE INVENTION

The present invention relates to novel piperazinophenylpropionic and piperazinophenoxyacetic acid derivatives, which are substituted on the piperazine ring by a phenyl or pyridyl radical carrying an amidino radical, and their salts and biolabile esters, and pharmaceutical preparations comprising these compounds and processes and intermediates for the preparation of these compounds.

Published European Patent Application No. EP 542,363 and published International Patent Application No. WO 93/14077 disclose derivatives of piperidinecarboxylic acids which inhibit fibrinogen-dependent blood platelet aggregation.

SUMMARY OF THE INVENTION

The object of the present invention is to develop novel pharmaceutical antithrombotic and blood platelet aggregation-inhibiting active compounds which have a favorable profile of action.

It has now been found that the novel piperazinophenylpropionic and piperazinophenoxyacetic acid derivatives according to the invention have useful pharmacological properties, exhibit antithrombotic and blood platelet aggregation-inhibiting effects on account of fibrinogen receptor-antagonistic properties and have a favorable profile of action with low toxicity and good tolerability. Due to their activity profile, the substances according to the invention are suitable as antithrombotic active compounds for the treatment of disease states based on thrombotic processes.

DETAILED DESCRIPTION OF THE PREFERRED EMBODIMENTS

The invention therefore relates to novel compounds of the general formula I

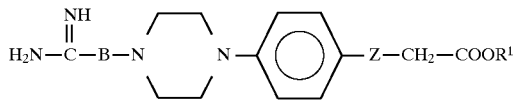

in which
Z is oxygen or a methylene group,
B is a phenyl or pyridyl radical,
$R^1$ is hydrogen or a group forming a biolabile ester, and
their physiologically acceptable acid addition salts and physiologically acceptable salts of acids of the formula I.

In the compounds of the formula I, Z can be a methylene group or oxygen and is preferably oxygen.

B can be a phenyl or pyridyl radical and is preferably phenyl. The amidino group bonded to B is preferably arranged in the para-position relative to the piperazine ring.

The compounds of the formula I are carboxylic acid derivatives optionally esterified by a group forming a biolabile ester. Suitable groups $R^1$ forming biolabile esters are those which can be removed under physiological conditions in vivo with liberation of the carboxylic acids.

Suitable groups $R^1$ forming biolabile esters include lower alkyl groups, phenyl or phenyl-lower alkyl groups optionally substituted in the phenyl ring by lower alkyl or by a lower alkylene chain bonded to two adjacent carbon atoms, or $C_2$–$C_6$-alkanoyloxy methyl groups optionally substituted on the oxymethyl group by lower alkyl. If the group $R^1$ forming a biolabile ester is or contains lower alkyl, this can be branched or unbranched and can contain 1 to 4, preferably 1 to 2, carbon atoms. If the group forming a biolabile ester is an optionally substituted phenyl-lower alkyl group, its alkylene chain can contain 1 to 3, preferably 1, carbon atom(s). If the phenyl ring is substituted by a lower alkylene chain, this can contain 3 to 4, in particular 3, carbon atoms. A suitable phenyl-containing substituent $R^1$ is, in particular, phenyl, benzyl or indanyl. If $R^1$ is an optionally substituted alkanoyloxy methyl group, its alkanoyloxy group can contain 2 to 6, preferably 3 to 5, carbon atoms, and is preferably branched and can be, for example, a pivaloyloxymethyl radical (=tert-butylcarbonyloxy-methyl radical).

According to the invention, the novel compounds of the formula I and their salts are obtained by hydrogenating, in a known manner, compounds of the general formula IIa and their salts

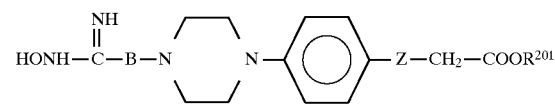

in which Z and B have the above meanings and $R^{201}$ is an acid protective group, to give compounds of the general formula III

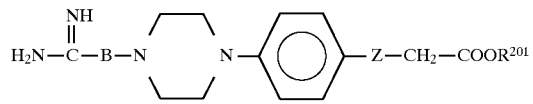

in which Z, B and $R^{201}$ have the above meanings, and, provided the acid protective group $R^{201}$ in the compounds of the formula III is not a desired group forming a biolabile ester, removing this acid protective group to liberate acids of the formula I or reacting the compounds of the formula III or acids of the formula I obtained therefrom with an alcohol of the general formula IVa

$$R^{101}\text{—OH} \qquad\qquad\qquad\qquad\qquad\text{IVa}$$

in which $R^{101}$ has the meaning indicated for $R^1$ with the exception of hydrogen, or its reactive derivatives, to give compounds of the formula Ia

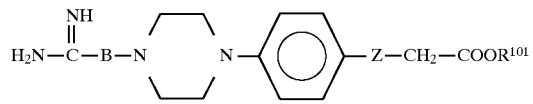

in which Z, B and $R^{101}$ have the above meanings, and, if desired, converting compounds of the formula I obtained into their physiologically acceptable acid addition salts or converting acids of the formula I into their physiologically acceptable salts or converting acid addition salts of the compounds of the formula I or salts of the acids of the formula I into the free compounds.

Suitable physiologically acceptable acid addition salts of the compounds of the formula I include, for example, their salts with inorganic acids such as sulfuric acid, phosphoric acids or hydrohalic acids, in particular hydrochloric acid, or with organic acids, for example lower aliphatic mono-, di- or tricarboxylic acids such as maleic acid, fumaric acid, lactic acid, tartaric acid, acetic acid optionally substituted by halogen, preferably trifluoroacetic acid, with citric acid or with sulfonic acids, for example lower alkanesulfonic acids such as methanesulfonic acid or benzenesulfonic acids optionally substituted in the benzene ring by halogen or lower alkyl, such as p-toluenesulfonic acid.

Free acids of the formula I can be present as acids and as zwitterions, in which a nitrogen atom present in the molecule is protonated by the proton of the carboxylic acid function. In the sense of the present invention, the formula I therefore includes both biolabile esters and free acids and the corresponding zwitterionic forms.

The hydrogenation of the hydroxyamidines of the formula IIa to give the amidines of the formula III can be carried out by customary methods for catalytic hydrogenation. Suitable hydrogenation catalysts include, for example, optionally partially inactivated noble metal catalysts such as palladium on active carbon. The reaction is carried out in an organic solvent which is inert under the reaction conditions. Suitable organic solvents include, for example, lower aliphatic ethers such as tetrahydrofuran or diethyl ether, lower alkanols such as methanol or ethanol, organic acids such as lower aliphatic monocarboxylic acids, for example acetic acid or its anhydride, or mixtures of the abovementioned solvents. A hydrogen pressure suitable for the hydrogenation is, for example, between 0.5 and 3 bar and is preferably between 1 and 2 bar. The hydrogenation is advantageously carried out at room temperature.

As a protective group $R^{201}$, customary protective groups for the protection of acidic functions can be selected, which are introduced by known methods and then removed again by known methods. Suitable acid protective groups are known, for example, from McOmie, "Protective Groups in Organic Chemistry", Plenum Press, and Greene, "Protective Groups in Organic Synthesis", Wiley Interscience Publication. The protective groups employed can also be groups forming a biolabile ester. In this case, the compounds of formula III obtained in the hydrogenation are already esters of formula Ia according to the invention.

The protective group $R^{201}$, provided it is not a desired group forming a biolabile ester in the compounds of the formula I, can be removed in a known manner from the compounds of formula III obtained by hydrogenation of the compounds of formula IIa.

Hydrolytically removable acid protective groups can advantageously be contained in the compounds of the formula III. Free acids of formula I can be obtained by hydrolytic cleavage of these compounds of formula III or of the esters of formula Ia, which is known per se. The hydrolysis is customarily carried out in aqueous medium under acidic reaction conditions, where acid addition salts of compounds of the formula I can be formed. Acids suitable for carrying out the hydrolysis include, for example, inorganic acids, such as hydrohalic acids, in particular hydrochloric acid, and also organic acids such as acetic acid optionally substituted by halogen, for example trifluoroacetic acid, or sulfonic acids, for example p-toluenesulfonic acid or methanesulfonic acid. For the acidic ester hydrolysis, if desired, polar aprotic solvents such as lower partially halogenated hydrocarbons, in particular methylene chloride, can also be used. Temperatures between room temperature and the boiling temperature of the solvent are suitable for carrying out the reaction.

For the preparation of esters of formula Ia, acids of formula Ia can be esterified in a known manner. For the esterification, the free acids of formula I or their acid addition salts or their reactive derivatives, such as mixed acid anhydrides with sulfonic acids, obtained by generally known processes can be reacted with alcohols of the formula IVa, or their reactive derivatives, under conditions suitable for ester formation. Acid-catalyzed esterification, for example, in an excess of the alcohol of formula IVa to be introduced, which can simultaneously also serve as a solvent, has proved suitable. The reaction can be carried out at temperatures which are between room temperature and the boiling temperature of the solvent. The acid employed to catalyze the esterification reaction can be an organic acid such as a sulfonic acid or an inorganic acid, for example a hydrohalic acid. In particular, the esterification can be carried out in 1-normal alcoholic hydrochloric acid solution.

The esterification of the free acids of formula I with reactive derivatives of alcohols of formula IVa can take place in a known manner. Suitable reactive derivatives of alcohols of the formula IVa include, for example, the halides which can be prepared from these alcohols in a known manner, preferably their chlorides or bromides, or their esters with lower alkanesulfonic acids such as methanesulfonic acid or with optionally substituted aromatic sulfonic acids such as benzenesulfonic acids.

Esters of formula Ia can also be obtained by reaction of esters of formula III with alcohols of formula IVa according to known methods for transesterification. The transesterification can advantageously take place in solution. A suitable solvent is an excess of an alcohol of the formula IVa which is to be esterified or a mixture of the alcohol of the formula IVa to be esterified with an organic solvent which is inert under the reaction conditions. Suitable starting compounds for the transesterification are all easily cleavable esters of the formula III, in particular the tert-butyl esters, which are easily cleavable in acidic medium. The above reaction temperatures and solvents suitable for the esterification of the free acids of the formula I can equally also be used for transesterification. For acidic catalysis of the transesterification, organic acids such as sulfonic acids or inorganic acids such as hydrohalic acids can be used. For example, the transesterification can be carried out in dilute alcoholic hydrohalic acids, in particular alcoholic hydrochloric acid solution, for example in 0.5 to 3 normal, preferably 1 to 2-normal, hydrochloric acid solution.

Compounds of formula I can be isolated from the reaction mixture and purified in a known manner. Acid addition salts can be converted into the free bases in a customary manner, and the latter can be converted, if desired, in a known manner into physiologically acceptable acid addition salts.

Compounds of the general formula IIb

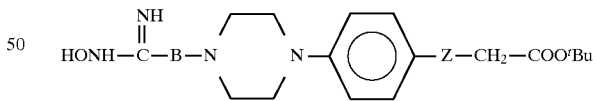

in which B and Z have the above meanings, can be obtained from the cyanides of the general formula V

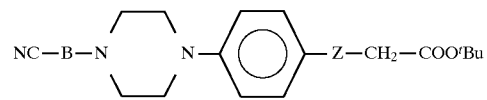

in which B and Z have the above meanings, by a known reaction with hydroxylamine or an appropriate salt thereof. For this purpose, a cyanide compound of the formula V can be reacted in a polar protic solvent, for example a lower alkanol, preferably methanol, with hydroxylamine or a salt thereof, advantageously hydroxylamine hydrochloride, in the presence of an organic base such as a lower alkali metal alkoxide, for example potassium tert-butoxide, at temperatures between room temperature and the boiling point of the solvent. In order to facilitate a reaction which is as rapid and complete as possible, it may be advantageous to work under anhydrous conditions at the boiling point of the solvent and in each case to add hydroxylamine hydrochloride and potassium tert-butoxide to the reaction mixture again at certain time intervals, for example every 4 hours, until reaction is complete.

From the compounds of the formula IIb, compounds of the general formula II

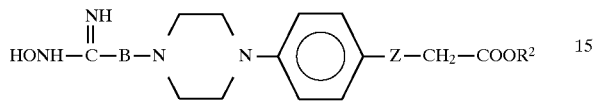

in which B and Z have the above meanings and $R^2$ is hydrogen or an acid protective group $R^{201}$, can be prepared by removing, provided the tert-butyl group in the compounds of the formula IIb is not the desired acid protective group, the tert-butyl group to liberate the acids of the formula II or reacting the compounds of the formula IIb or acids of the formula II obtained therefrom with an alcohol of the general formula IVb $$R^{201}\text{—OH} \qquad \qquad \text{IVb}$$

in which $R^{201}$ has the above meaning, or its reactive derivatives, to give compounds of the formula IIa. If desired, compounds of the formula II obtained can be converted into their physiologically acceptable salts or acid addition salts of the compounds of the formula II or salts of the acids of the formula II can be converted into the free compounds. Suitable reactive derivatives of the alcohols of the formula IVb are the reactive derivatives indicated above for alcohols of the formula IVa.

Suitable physiologically acceptable acid addition salts of the compounds of the formula II are the acid addition salts indicated above for compounds of the formula I.

Free acids of the formula II can be present as acids and as zwitterions, in which a nitrogen atom present in the molecule is protonated by the proton of the carboxylic acid function. In the sense of the present invention, the formula II therefore includes both acids protected by acid protective groups and free acids and the corresponding zwitterionic forms.

For the preparation of compounds of the formula II from the compounds of the formula IIb, suitable methods are those indicated above for the preparation of the compounds of the formula I from compounds of the formula III.

Cyanides of the formula V, in which Z is the methylene group, can be obtained by reacting the compound of the formula VI

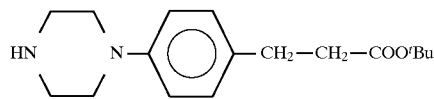

with the compounds of the general formula VII $$X^1\text{—B—CN} \qquad \qquad \text{VII}$$

in which B has the above meaning and $X^1$ is a removable reactive group such as halogen, in particular chlorine or fluorine, in a known manner. Customarily, the reaction is carried out in an organic, polar aprotic solvent, for example dimethyl sulfoxide, dimethylformamide, acetonitrile or N-methyl-2-pyrrolidone at temperatures between room temperature and 150° C., preferably between 100° and 140° C. To optimize the reaction conditions, a weak base, e.g. an alkali metal carbonate such as potassium carbonate or lithium carbonate, can advantageously be added. Further, it may be advantageous after a certain reaction time, for example after 5 to 7 hours, to add a certain amount of the compound of the formula VII again in order to complete the conversion.

The compound of the formula VI can be obtained in a known manner by reaction of the compound of formula VIII

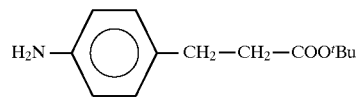

with bis-2-chloroethylamine of the formula IX

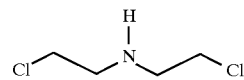

or an appropriate salt thereof, in particular its hydrochloride. Advantageously, the reaction is carried out in the presence of an acid-binding reagent such as an organic weakly nucleophilic basic nitrogen compound, for example 2,6-lutidine, pyridine or collidine, in a solvent which is inert under the reaction conditions at temperatures between room temperature and 180° C., preferably between 120° and 160° C. Suitable solvents include aromatic solvents such as optionally substituted benzenes, for example benzene, toluene, xylene or chlorobenzene.

The compound of formula VIII can be obtained by catalytic hydrogenation in a known manner of tert-butyl 4-nitrocinnamate of the formula X

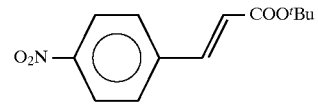

under the reaction conditions indicated above for the catalytic hydrogenation of the compounds of formula II to give the amidines of the formula III, preferably in lower alkanols such as methanol as solvents.

The ester of formula X can be prepared by reaction of 4-nitrocinnamoyl chloride with tert-butanol by known methods of carboxylic acid esterification.

Cyanides of formula V in which Z is oxygen can be prepared from the substituted hydroxybenzenes of the general formula XI

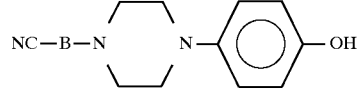

in which B has the above meaning, by the known reaction with the tert-butyl esters of the general formula XII $$X^2\text{—CH}_2\text{—COO}^t\text{Bu} \qquad \qquad \text{XII}$$

in which $X^2$ is a removable reactive group. $X^2$ can be, for example, a radical of an aliphatic or of an aromatic sulfonic acid optionally substituted in the phenyl ring by lower alkyl or halogen, such as a p-toluenesulfonyloxy, phenylsulfonyloxy or a methanesulfonyloxy radical, or a halogen atom, in particular bromine or chlorine. Preferably $X^2$ is chlorine. Advantageously, the coupling reaction of the compounds of formula XI with compounds of formula XII can be carried out under the conditions indicated above for the reaction of the compounds of formula VI with compounds of formula VII, preferably at room temperature.

The compounds of the formula XI can be prepared in a known manner by reacting compounds of the general formula XIII

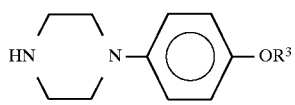

in which $R^3$ is hydrogen or a suitable protective group for the alcohol function, with the compounds of formula VII and then removing an optional protective group $R^3$. The coupling reaction of the compounds of formula XIII with compounds of formula VII can be carried out under the conditions described above for the reaction of the compounds of formula VI with compounds of formula VII, preferably at temperatures of 60° to 90° C. Provided $R^3$ is hydrogen in the compounds of the formula XIII, the use of lithium carbonate as a weak base is preferred.

If $R^3$ in compounds of the formula XIII is an alcohol protective group, suitable protective groups include those which can preferably be removed again under reductive conditions. Suitable protective groups are known, for example, from McOmie, "Protective Groups in Organic Chemistry", Plenum Press. In particular, $R^3$ can be a lower alkenyl group such as the 2-propenyl group. This can be removed using known methods for the reductive cleavage of allyl ethers. The reducing agent used can be, for example, a mixture of formic acid and triethylamine. The reductive cleavage of the allyl ether can be carried out, for example, in a polar solvent such as a mixture of acetonitrile and water and in the presence of a catalyst such as a palladium(II) salt, for example palladium acetate, and triphenylphosphine. The reaction can be carried out between room temperature and the boiling point of the reaction mixture.

The compound of formula XIII in which $R^3$ is hydrogen is 1-(4-hydroxyphenyl)piperazine, which is known per se.

Compounds of the general formula XIIIa

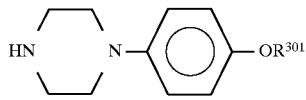

in which $R^{301}$ has the meaning of $R^3$ with the exception of hydrogen, can be prepared by the known reaction of amines of the general formula XIV

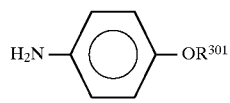

in which $R^{301}$ has the above meaning, with bis-2-chloro-ethylamine of formula IX under the conditions indicated above for the reaction of the compounds of formula VIII with compounds of formula IX.

The amines of the general formula XIV can be liberated by hydrolysis in a known manner from the acetamides of the general formula XV

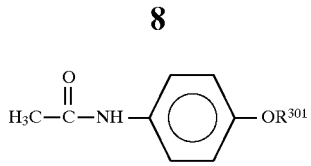

in which $R^{301}$ has the above meaning, for example by boiling for several hours in acidic alcoholic medium, such as a mixture of concentrated hydrochloric acid and ethanol.

The compounds of formula XV can be prepared by reaction of 4-acetamidophenol of the formula XVI

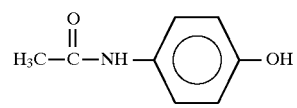

with a reagent suitable for the formation of an alcohol protective group in a known manner. In particular, the compound of the formula XVI can be converted with allyl bromide into an allyl ether by methods known for this purpose.

The compounds of the formula I and their pharmacologically acceptable salts are distinguished by interesting pharmacological properties. In particular, the substances exert an inhibitory action on the binding of fibrinogen to the fibrinogen receptor of the blood platelets, the glycoprotein IIb/IIIa (abbreviated as GP IIb/IIIa), and are thus suitable as blood platelet aggregation-inhibiting and antithrombotic active compounds for the prophylaxis and treatment of cardiovascular symptoms based on blood platelet aggregation processes, such as, for example, thromboses, arterioscleroses and cardiac or cerebral infarcts. Blood platelet aggregation plays an essential part in blood clotting and the formation of blood platelet thrombi and also occurs, inter alia, in thrombotic processes, which can lead to blockage of blood vessels and cardiovascular infarcts. An essential step in the formation of blood platelet thrombi is the binding of fibrinogen to the blood platelet membrane protein GP IIb/IIIa, blood platelets being cross-linked with one another by the bivalent fibrinogen. On account of their fibrinogen receptor-antagonistic properties, the substances according to the invention display marked antithrombotic actions and are distinguished by a favorable activity profile and good oral activity.

The inhibitory action of the substances of the formula I on the fibrinogen binding to the fibrinogen receptor of the blood platelets, the GP IIb/IIIa, was detected in a solid phase enzyme immunoassay of the ELISA type ("Enzyme-Linked Immunosorbent Assay") according to the method described by Kouns et al. (Blood 80 (1992) 2539–2547).

DESCRIPTION OF THE PHARMACOLOGICAL TEST METHOD

A solution of purified GP IIb/IIIa fibrinogen receptor from human blood platelets (1 µg/ml in phosphate-buffered physiological saline solution, pH 7.4) was applied in portions of 100 µl/sample position to a microtitre plate and allowed to stand at 4° C. for 18 hours. Excess receptor reagent was washed off by a standard wash (3 times 350 µl of wash buffer solution/sample position: 0.01% (v/v) Tween 80 in phosphate-buffered physiological saline solution) and unoccupied residual protein binding sites were occupied by a blocking reagent [300 µl/sample position of an aqueous receptor buffer solution: 20 mmole/liter of tris (hydroxymethyl)aminomethane, 150 mmole/liter of NaCl, 1 mmole/liter of $MgCl_2$, 1 mmole/liter of $CaCl_2$; treated with 5% (w/v) bovine serum albumin (BSA)]. The mixture was incubated at 37° C. for 2 hours and excess blocking reagent was removed.

Purified human plasma fibrinogen [100 μl/sample position of a 20 μg/ml solution in test buffer. Test buffer=receptor buffer mixed with 1% (w/v) BSA] was then added together with the test substance dissolved therein (concentration dependent on the test substance) and incubated at 37° C. for 2 hours. Unbound fibrinogen was removed by standard washing and the incubation was continued for a further hour at room temperature after addition of biotinylated rabbit antibodies against human fibrinogen (100 μl/sample position in optimum use dilution, dissolved in test buffer) . After a further standard wash, horseradish peroxidase-conjugated streptavidin (1:2000, in suitable dilution in test buffer) was added, and the mixture was incubated again at room temperature for one hour, followed by a further standard wash.

Finally, the peroxidase substrate 2,2'-azinodi-(3-ethylbenzothiazolinesulfonate) (abbreviated below as ABTS), (100 μl/sample position of a solution of 0.4 g/liter of ABTS in 0.1 mole/liter of citric acid buffer, adjusted to pH 4 using 0.4 mole/liter of $NaH_2PO_4 \cdot 2 H_2O$), treated with 0.003% (w/v) hydrogen peroxide, was added and the extinction of the mixture was measured at 405 nm at 5 minute intervals for twenty minutes.

The peroxidase activity was determined from the measurements as the increase in the extinction with time. It was used to calculate the total fibrinogen binding and also the non-specific fibrinogen binding. The non-specific fibrinogen binding was determined without addition of the GP IIb/IIIa. The specific fibrinogen binding could be calculated from these two values. The effect of the test substances was expressed in $IC_{50}$ values, which were obtained by interpolation from concentration-dependent measuring curves. The $IC_{50}$ is that concentration in μmole/liter at which a test substance inhibits the specific fibrinogen binding of GP IIb/IIIa by 50%. The following Table 1 presents the $IC_{50}$ values found for the test substance as negative common logarithms, the $pIC_{50}$ values. The example numbers relate to the subsequent preparation examples.

TABLE 1

| Test Substance Example No. | $pIC_{50}$ |
|---|---|
| 2a | 8.80 |
| 6 | 8.81 |
| 7 | 7.44 |
| 10 | 7.52 |
| 12 | 7.55 |

The test results described above show that the compounds of the formula I have a marked inhibitory action on the binding of fibrinogen to the fibrinogen receptor of the blood platelets, the GP IIb/IIIa, and are therefore suitable for favorably affecting blood platelet aggregation processes based on pathological conditions, in particular thrombotic processes.

The advantageous pharmacological properties of the compounds according to the invention can also be detected in standard animal experiments, for example by the inhibition of the ADP-induced thrombi formation in the microcirculation of hamster cheeks.

Due to their above-described action, the compounds of the formula I are suitable as medicaments for larger mammals, in particular man, for the treatment of cardiovascular symptoms such as, for example, thromboses, arterioscleroses and cardiac or cerebral infarcts. The doses to be used can be individually different and of course vary depending on the type of the condition to be treated, the substance used and the administration form. In general, however, pharmaceutical forms having an active compound content of 1 to 200 mg per individual dose are suitable for administration to larger mammals, in particular man.

As therapeutics, the compounds of the formula I can be contained in pharmaceutical preparations, for example, tablets, capsules, suppositories or solutions, with customary pharmaceutical auxiliaries. These pharmaceutical preparations can be prepared by known methods using customary solid or liquid excipients, such as, for example, lactose, starch or talc, or liquid paraffins and/or using customary pharmaceutical auxiliaries, for example tablet disintegrants, solubilizers or preservatives.

The following examples are intended to illustrate the invention in greater detail, without restricting its scope.

The structures of the novel compounds were confirmed by spectroscopic investigations, in particular by analysis of the NMR, mass or IR spectra.

EXAMPLE 1:

tert-Butyl 4- [4- (4-amidinophenyl) -1-piperazinyl] phenoxyacetate.

A) 15.1 g of 1-(4-hydroxyphenyl)piperazine, 9.4 g of lithium carbonate and 10.4 g of 4-fluorobenzonitrile in 250 ml of dimethyl sulfoxide were reacted at 80° C. for 4 hours under a nitrogen atmosphere. After fresh addition of 3.0 g of 4-fluorobenzonitrile, the mixture was heated at 80° C. for a further 4 hours and the precipitated product was filtered out with suction after cooling the reaction mixture. To separate the co-precipitated lithium carbonate, the crude product was then stirred with aqueous citric acid. After filtering out with suction and drying in a vacuum oven at 60° C., 18.7 g of 4-[4-(4-cyanophenyl)-1-piperazinyl]phenol were obtained, m.p.=258°–262° C.

B) 17.2 g of tert-butyl chloroacetate, 15.9 g of potassium carbonate and 160 mg of potassium iodide were added at room temperature to a solution of 16.0 g of the phenol obtained above in 150 ml of dimethylformamide. After 13 hours, a further 7.0 g of potassium carbonate and 8.0 g of tert-butyl chloroacetate were added and the mixture was stirred for a further 2 hours. After addition of 1500 ml of ethyl acetate, the mixture was washed 3 times with 300 ml of water each time, then the organic phase was separated and dried over magnesium sulfate. After filtering out the drying agent, the mixture was concentrated to a total volume of 200 ml, and the product which crystallized out as a result was filtered out, washed with diethyl ether and dried in vacuo over potassium hydroxide. 18.5 g of tert-butyl 4-[4-(4-cyanophenyl)-1-piperazinyl]phenoxyacetate was obtained.

C) A solution of 17.5 g of the tert-butyl ester obtained above in 1750 ml of methanol was heated to reflux under a nitrogen atmosphere. After 10 minutes, 1.55 g of hydroxylamine hydrochloride and 2.5 g of potassium tert-butoxide were added, while the solution was further boiled with reflux cooling. At intervals of 4 hours in each case, 6 further portions of hydroxylamine hydrochloride and potassium tert-butoxide were added. After reaction was complete, the mixture was allowed to cool to room temperature, diluted with 300 ml of methylene chloride and washed with saturated potassium carbonate solution. Finally, the organic phase was separated off, dried over magnesium sulfate and concentrated. The resulting white crystals of tert-butyl 4-[4-

(4-hydroxyamidinophenyl)-1-piperazinyl]phenoxyacetate were dried at 60° C. The yield was 11.3 g; m.p.>240° C. (decomposition).

D) 10.5 g of the hydroxyamidine obtained above were dissolved in 200 ml of a mixture of glacial acetic acid and acetic anhydride and the batch was flushed with nitrogen. 2.0 g of 10% palladium catalyst an active carbon were then added, and the mixture was hydrogenated at room temperature and a hydrogen pressure of 1 bar for 6 hours. After filtering out the catalyst, the solvent was removed by azeotropic distillation using toluene, and the residue which remained was recrystallized from methanol. 10.0 g of an acetate of the title compound having a content of about 0.7 mole of acetic acid were obtained. M.p.>270° C. (decomposition).

EXAMPLE 2:

4-[4-(4-Amidinophenyl)-1-piperazinyl]-phenoxyacetic acid.

2a) 5.0 g of tert-butyl 4-[4-(4-amidinophenyl)-1-piperazinyl]phenoxyacetate·0.7 acetate (preparation see Example 1) were dissolved in 120 ml of 6-normal aqueous hydrochloric acid and the solution was stirred at room temperature for one hour. The resulting product was filtered out with suction, washed with a little water and dried at 50° C. in a vacuum drying oven. 3.7 g of the dihydrochloride of the title compound were obtained; m.p.>340° C.

2b) 12.0 g of tert-butyl 4-[4-(4-amidinophenyl)-1-piperazinyl]phenoxyacetate·0.7 acetate were dissolved in 200 ml of a mixture of methylene chloride and trifluoroacetic acid (2:1). After stirring at room temperature for 5 hours, the readily volatile components were stripped off in vacuo, the residue was treated 3 times with 25 ml of toluene in each case and the mixture was concentrated again in each case. The resulting residue was taken up using a mixture of methanol and methylene chloride (1:4), and the product was precipitated by addition of hexane. After filtering and drying, 12.0 g of a brown powder were obtained, which was dissolved with heating in a mixture of methanol and methylene chloride. After cooling to room temperature, the product was precipitated again with hexane. 7.25 g of the bistrifluoroacetate of the title compound were obtained, which was further purified by means of preparative high performance liquid chromatography (HPLC); m.p.>340° C.

EXAMPLE 3:

Methyl 4-[4-(4-amidinophenyl)-1-piperazinyl]-phenoxyacetate.

3a) A solution of 1.0 g of tert-butyl 4-[4-(4-amidinophenyl)-1-piperazinyl]phenoxyacetate·0.7 acetate in 60 ml of 1-normal methanolic hydrochloric acid was stirred at room temperature for 40 hours. Crystallization was completed by allowing to stand overnight in a refrigerator. The precipitated product was filtered off with suction, washed and dried. 900 mg of the dihydrochloride of the title compound were obtained; m.p.>330° C.

3b) 100 mg of the dihydrochloride of 4-[4-(4-amidinophenyl)-1-piperazinyl]-phenoxyacetic acid (preparation see Example 2a) were suspended in 15 ml of 1-normal methanolic hydrochloric acid, and the mixture was stirred at room temperature for about 3 hours, a clear solution forming with increasing reaction time. The reaction mixture was concentrated and dried over potassium hydroxide in a desiccator. 100 mg of the trishydrochloride of the title compound were obtained; m.p.>330° C.

EXAMPLE 4:

tert-Butyl 3-{4-[4-(4-amidinophenyl)-1-piperazinyl]phenyl}propionate.

A) A solution of 17.8 g of 4-nitrocinamoyl chloride in 200 ml of tetrahydrofuran was added dropwise to a catalytic amount of 4-pyrrolidinopyridine and 6.7 ml of pyridine in 900 ml of tert-butanol. After addition was complete, the mixture was diluted with a further 200 ml of tetrahydrofuran and stirred at room temperature for a further 5 hours. After filtering out the deposited precipitate, the filtrate was diluted to 2 liters using methyl tert-butyl ether and washed first 2 times with saturated sodium hydrogencarbonate solution, then 2 times with saturated sodium chloride solution. Drying and concentration of the organic phase yielded 18.0 g of crystalline tert-butyl 4-nitrocinnamate.

B) 20.0 g of the 4-nitrocinnamic acid ester obtained as described above were suspended in 500 ml of methanol, treated with 2.0 g of 10% strength palladium on active carbon and hydrogenated at room temperature and a pressure of 4 bar for 15 hours. After filtering out the catalyst, the mixture was concentrated and 15.0 g of tert-butyl 4-aminophenylpropionate were obtained, which was employed without further purification and characterization for the following reaction.

C) A solution of 11.0 g of the aminophenylpropionic acid ester obtained above, 10.0 g of bis (2-chloroethyl) amine hydrochloride and 13 ml of collidine in 150 ml of chlorobenzene were stirred at 140° C. for 6 hours. After cooling, the precipitated crystals were filtered out, and the mother liquor was concentrated. Chromatography on silica gel yielded 6.7 g of tert-butyl 3-[4-(1-piperazinyl)phenyl]propionate.

D) 4.3 g of the piperazinylphenylpropionic acid ester obtained above, 1.8 g of fluorobenzonitrile and 3.0 g of potassium carbonate were dissolved in 100 ml of N-methylpyrrolidone, and the mixture was stirred at 120° C. for 7 hours. After addition of a further 0.4 g of 4-fluorobenzonitrile, the mixture was heated to 120° C. again for 7 hours. The precipitated salts were filtered out, and the mother liquor was evaporated. The residue was dissolved in methylene chloride and the solution was washed with water. Concentration and crystallization from ethanol yielded 3.0 g of tert-butyl 3-{4-[4-(4-cyanophenyl)-1-piperazinyl]phenyl}-propionate.

E) 3.0 g of the phenylpropionic acid ester obtained under D) were reacted with 4 times 0.25 g of hydroxylamine hydrochloride and 4 times 0.38 g of potassium tert-butoxide according to the method described in Example 1C). 1.20 g of tert-butyl 3-{4-[4-(4-hydroxyamidino-phenyl)-1-piperazinyl]phenyl}propionate were obtained after recrystallization from methanol/methylene chloride.

F) 0.85 g of the hydroxyamidine obtained above under E) and 0.30 g of 10% palladium catalyst on active carbon were reacted according to the method described in Example 1D). 0.35 g of the acetate of the title compound was obtained. IR: 2977, 1725, 1608 $cm^{-1}$

EXAMPLE 5:

tert-Butyl 4-{4-[2-(5-amidinopyridyl)]-1-piperazinyl}phenoxyacetate.

A) 1.0 g of 1-(4-hydroxyphenyl)piperazine, 650 mg of lithium carbonate and 780 mg of 2-chloropyridine-5-carbonitrile were dissolved in 30 ml of dimethyl sulfoxide and reacted at 80° C. for 3 hours under a nitrogen atmosphere. After cooling, the mixture was concentrated, and the oil obtained was stirred in 100 ml of 2-molar citric acid solution for 30 minutes, the product crystallizing out. After filtration it was washed with water and subsequently dried. Extraction of the filtrate with 100 ml of ethyl acetate yielded further product, which was combined with the main amount. The yield was 1.5 g of 4-{4-[2-(5-cyanopyridyl)]-1-piperazinyl}phenol.

B) 3.5 g of the substituted phenol obtained above were dissolved in 40 ml of dimethylformamide together with 3.6 ml of tert-butyl chloroacetate, 3.45 g of potassium carbonate and 25 mg of potassium iodide, and the mixture was stirred at room temperature for 9 hours under a nitrogen atmosphere. After reaction had taken place, the mixture was diluted with ethyl acetate and washed 3 times with water. The combined organic phases were dried over sodium sulfate and concentrated. 4.6 g of 4-{4-[2-(5-cyanopyridyl)]-1-piperazinyl}phenoxy-acetate were obtained.

C) A solution of 4.5 g of the phenoxyacetic acid ester obtained above in 200 ml of absolute methanol was heated to boiling under a nitrogen atmosphere and with reflux cooling. After 10 minutes, 400 mg of hydroxylamine hydrochloride and 640 mg of potassium tert-butoxide were added, then further portions of hydroxylamine hydrochloride and potassium tert-butoxide were added at intervals of 4 hours until reaction was complete. After cooling to room temperature, the mixture was diluted with methylene chloride and washed with 5% strength potassium carbonate solution. The organic phase was dried and concentrated in vacuo. For purification, it was recrystallized from a mixture of ethyl acetate and methanol (1:1). 3.6 g of tert-butyl 4-{4-[2-(5-hydroxyamidinophenyl)]-1-piperazinyl}-phenoxyacetate were obtained.

D) 3.1 g of the product obtained above were dissolved in 100 ml of a mixture of glacial acetic acid and acetic anhydride (99:1). The mixture was flushed with nitrogen, then 1.0 g of 10% strength palladium catalyst on active carbon was added, and it was hydrogenated at a pressure of 1 bar for 4 hours. The catalyst was filtered out and washed with toluene, and the filtrate was concentrated. Residual solvent was removed by azeotropic distillation using toluene. Crystallization from a mixture of ethyl acetate and methanol (2:1) yielded 2.7 g of the monoacetate of the title compound, m.p.>217° C. (decomposition).

EXAMPLE 6:

4-{4-[2-(5-Amidinopyridyl)]-1-piperazinyl}-phenoxyacetic acid.

2.0 g of tert-butyl 4-{4-[2-(5-amidinopyridyl)]-1-piperazinyl}phenoxyacetate monoacetate (preparation see Example 5) were dissolved in 20 ml of 6-normal aqueous hydrochloric acid, and the solution was stirred at room temperature for 1 hour. The trishydrochloride of the title compound which crystallized out was filtered out, washed with a little water and then dried. Yield: 1.6 g, m.p.=300° C. (decomposition).

EXAMPLE 7:

Methyl 4-{4-[2-(5-amidinopyridyl)]-1-piperazinyl}phenoxyacetate.

353 mg of 4-{4-[2-(5-amidinopyridyl)]-1-piperazinyl}-phenoxyacetic acid trishydrochloride (preparation see Example 6) were taken up using 26 ml of 1-normal methanolic hydrochloric acid, and the solution was stirred at room temperature for 3 hours. The precipitated product was filtered out with suction, washed with cold methanol and dried. 310 mg of the trishydrochloride of the title compound were obtained; m.p.=151°–154° C.

EXAMPLE 8:

Isopropyl 4-{4-[2-(5-amidinopyridyl)]-1-piperazinyl}phenoxyacetate.

460 mg of tert-butyl 4-{4-[2-(5-amidinopyridyl)]-1-piperazinyl}phenoxyacetate monoacetate (preparation see Example 5) were taken up using 26 ml of a 2-normal solution of hydrochloric acid in isopropanol, and the solution was stirred at 90° C. for 3 hours. The precipitated product was filtered out with suction, washed with cold isopropanol and dried. 360 mg of the trishydrochloride of the title compound were obtained, m.p.=157°–162° C.

EXAMPLE 9:

tert-Butyl 3-{4-[4-(2-(5-amidinopyridyl))-1-piperazinyl]phenyl}propionate.

A) 4.3 g of tert-butyl 4-(1-piperazinyl)phenylpropionate (preparation see Example 4C) were dissolved in 100 ml of N-methylpyrrolidone together with 2.08 g of 2-chloropyridine-5-carbonitrile and 3.0 g of potassium carbonate, and the mixture was heated at 120° C. for 5 hours. The precipitated salts were filtered out, and the mixture was then evaporated. The residue was taken up using methylene chloride and washed with water. After drying, it was concentrated, and the residue was crystallized from a mixture of isopropanol and ethanol. 3.85 g of tert-butyl 3-{4-[4-(2-(5-cyanopyridyl))-1-piperazinyl]phenyl}propionate were obtained.

B) 3.80 g of the tert-butyl ester obtained under A), 4 times 0.32 g of hydroxylamine hydrochloride and 4 times 0.48 g of potassium tert-butoxide were reacted according to the method described in Example 1C). The yield was 1.80 g of tert-butyl 3-{4-[4-(2-(5-hydroxyamidinopyridyl))-1-piperazinyl]phenyl}propionate after recrystallization from methanol/methylene chloride.

C) 1.0 g of the hydroxyamidine obtained above and 0.3 g of 10% strength palladium catalyst on active carbon were reacted according to the method described in Example 1D). 0.79 g of the acetate of the title compound was obtained. IR: 2977, 1724, 1607 cm$^{-1}$.

EXAMPLE 10:

3-{4-[4-(2-(5-Amidinopyridyl))-1-piperazinyl]-phenyl}propionic acid.

320 mg of tert-butyl 3-{4-[4-(2-(5-amidinopyridyl))-1-piperazinyl]phenyl}propionate (preparation see Example 9) were stirred at room temperature for 20 hours in 10 ml of 50% strength aqueous trifluoroacetic acid solution, and the solution was then evaporated in vacuo. The resulting crude product was purified by medium pressure liquid chromatography (MPLC) on a reversed phase silica gel (RP18). The yield of tetrakistrifluoroacetate of the title compound was 320 mg, m.p.=280° C. (decomposition).

The compounds of the formula I shown in the following Table 2 can also be prepared by the processes described in the above examples.

TABLE 2

| Example No. | B | Z | R¹ | salt | m.p. = |
|---|---|---|---|---|---|
| 11 | 1,4-phenyl | O | i-Pr | 2 HCl | 268° C. |
| 12 | 1,4-phenyl | CH₂ | H | 2 HCl | 290° C. |
| 13 | 1,4-phenyl | O | H | 2 p-TsOH | 270–274° C. |
| 14 | 1,4-phenyl | O | H | 2 MsOH | 272–275° C. |
| 15 | 1,4-phenyl | O | H | 2 PhSO₃H | 236–239° C. | iPr = isopropyl; p-TSOH = p-toluenesulfonic acid; MsOH = methanesulfonic acid; Ph = C₆H₅-

Example of a Pharmacological Formulation

Example:

Tablets comprising 4- [4- (4-Amidinophenyl) -1-piperazinyl]phenoxyacetic acid dihydrochloride.

Tablets were prepared having the following composition per tablet:

| | |
|---|---|
| 4-[4-(4-Amidinophenyl)-1-piperazinyl]-phenoxyacetic acid dihydrochloride | 20 mg |
| Corn starch | 60 mg |
| Lactose | 135 mg |
| Gelatin (as a 10% strength solution) | 6 mg |

The active compound, the corn starch and the lactose were thickened with the 10% strength gelatin solution. The paste was comminuted and the resulting granules were put on a suitable plate and dried at 45° C. The dried granules were fed into a pulverizing machine and mixed with the following further auxiliaries in a mixer:

| | |
|---|---|
| Talc | 5 mg |
| Magnesium stearate | 5 mg |
| Corn starch | 9 mg | and then compressed to give tablets of 240 mg.

The foregoing description and examples have been set forth merely to illustrate the invention and are not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A compound corresponding to the formula I:

$$H_2N-\overset{NH}{\underset{\parallel}{C}}-B-N\diagup\hspace{-0.3em}\diagdown N-\bigcirc-Z-CH_2-COOR^1$$

wherein

Z is oxygen or a methylene group,

B is a phenyl or pyridyl group,

R¹ is hydrogen or a group forming a biolabile ester, or a physiologically acceptable acid addition salt thereof, or a physiologically acceptable salt of an acid of formula I.

2. A compound according to claim 1, wherein the group R¹ is a lower alkyl group.

3. A compound according to claim 1, wherein R¹ is hydrogen.

4. A compound according to claim 1, wherein Z is oxygen.

5. A compound according to claim 1, wherein B is a phenyl ring.

6. A compound according to claim 5, selected from the group consisting of 4- [4- (4-Amidinophenyl) -1-piperazinyl]-phenoxyacetic acid, lower alkyl esters thereof, physiologically acceptable acid addition salts of said acid or esters, and physiologically acceptable salts of said acid.

7. A pharmaceutical composition comprising an effective fibrinogen receptor antagonizing amount of a compound according to claim 1, and a pharmaceutical carrier or adjuvant.

8. A process for preparing a compound corresponding to the formula I:

$$H_2N-\overset{NH}{\underset{\parallel}{C}}-B-N\diagup\hspace{-0.3em}\diagdown N-\bigcirc-Z-CH_2-COOR^1$$

wherein

Z is oxygen or a methylene group,

B is a phenyl or pyridyl radical, and

R¹ is hydrogen or a group forming a biolabile ester, or a physiologically acceptable acid addition salt thereof or a physiologically acceptable salt of an acid of formula I, said process comprising:

hydrogenating a compound corresponding to formula IIa $$HONH-\overset{NH}{\underset{\parallel}{C}}-B-N\diagup\hspace{-0.3em}\diagdown N-\bigcirc-Z-CH_2-COOR^{201}$$

wherein Z and B have the foregoing meanings and R²⁰¹ is an acid protective group, to form a compound corresponding to the formula III $$H_2N-\overset{NH}{\underset{\parallel}{C}}-B-N\diagup\hspace{-0.3em}\diagdown N-\bigcirc-Z-CH_2-COOR^{201}$$

wherein Z, B and R²⁰¹ have the foregoing meanings, and, provided the acid protective group R²⁰¹ in the compound of formula III is not a desired group forming a biolabile ester, removing the acid protective group to liberate the acid of formula I, and if R¹ is other than hydrogen, reacting the compound of formula III or acid of formula I obtained therefrom, or a reactive derivative thereof, with an alcohol corresponding to the formula IVa $$R^{101}-OH \qquad\qquad IVa$$

wherein R¹⁰¹ has the meaning indicated for R¹ with the exception of hydrogen, to form a compound corresponding to formula Ia $$H_2N-\overset{NH}{\underset{\parallel}{C}}-B-N\diagup\hspace{-0.3em}\diagdown N-\bigcirc-Z-CH_2-COOR^{101}$$

wherein which Z, B and R¹⁰¹ have the foregoing meanings.

9. A process according to claim 8, further comprising the step of converting a free base of formula I into a corresponding physiologically acceptable acid addition salt.

10. A process according to claim 8, further comprising the step of converting an acid of formula I into a corresponding physiologically acceptable salt.

11. A process according to claim 8, further comprising the step of converting an acid addition salt of a compound of formula I or a salt of an acid of formula I into a corresponding free base.

12. A compound corresponding to the formula II

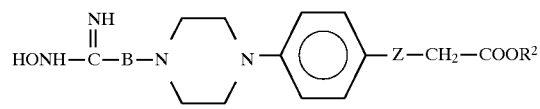

wherein
 Z is oxygen or a methylene group,
 B is a phenyl or pyridyl group, and
 $R^2$ is hydrogen or an acid protective group, or an acid addition salt thereof, or a salt of an acid of formula II.

* * * * *